(12) United States Patent
Pirzad (10) Patent No.: US 7,807,103 B2
(45) Date of Patent: Oct. 5, 2010

(54) ALLERGEN DETECTION APPARATUS (75) Inventor: Ramin Pirzad, St. Ives (GB)

(73) Assignee: Life Safety Distribution AG, Uster (CH)

( * ) Notice: Subject to any disclaimer, the term of this patent is extended or adjusted under 35 U.S.C. 154(b) by 236 days.

(21) Appl. No.: 11/451,975

(22) Filed: Jun. 12, 2006

(65) Prior Publication Data

US 2006/0228760 A1  Oct. 12, 2006

Related U.S. Application Data (62) Division of application No. 10/009,109, filed as application No. PCT/GB00/02100 on Jun. 9, 2000, now Pat. No. 7,195,922.

(30) Foreign Application Priority Data

Jun. 11, 1999  (GB) ................. 9913487.6

(51) Int. Cl.
    *G01N 21/00* (2006.01)
(52) U.S. Cl. .............. 422/56; 422/55; 422/57; 422/58; 422/61; 436/86; 436/164; 436/166; 436/169; 436/805; 436/808; 435/7.4; 435/23
(58) Field of Classification Search ........... 436/86, 436/164, 166, 169, 805, 808, 903; 422/61; 435/7.4, 23

See application file for complete search history.

(56) References Cited

U.S. PATENT DOCUMENTS

| | | | |
|---|---|---|---|
| 2,370,683 A * | 3/1945 | Palma ............... | 422/61 |
| 4,806,490 A | 2/1989 | Bischoff et al. | |
| 4,849,337 A | 7/1989 | Calenoff et al. | |
| 5,091,318 A | 2/1992 | Anawis et al. | |
| 5,464,739 A * | 11/1995 | Johnson et al. ......... | 435/4 |
| 5,500,375 A | 3/1996 | Lee-Own et al. | |
| 5,679,535 A | 10/1997 | Joyce et al. | |
| 5,731,157 A | 3/1998 | Miller et al. | |
| 5,766,933 A | 6/1998 | El Shami et al. | |
| 5,780,239 A * | 7/1998 | Carter et al. ........... | 435/7.1 |

(Continued)

FOREIGN PATENT DOCUMENTS

JP  60 147651  8/1985

(Continued)

OTHER PUBLICATIONS

Cayot, P. and Tainturier, G., "The Quantification of Protein Amino Groups by the Trinitrobenzene-sulfonic Acid Method: A Reexamination," Analytical Biochemistry, vol. 249, pp. 184-200 (1997).

(Continued)

*Primary Examiner*—Lyle A Alexander
*Assistant Examiner*—Dennis M White
(74) *Attorney, Agent, or Firm*—Husch Blackwell Sanders Welsh & Katz (57) ABSTRACT

A method of determining allergen activity in dust comprises: providing a dust sample; extracting from the dust sample at least one breakdown component or proteins or peptides; reacting the extracted at least one breakdown component with a colorimetric amine detection reagent such as TNBSA; and quantitatively measuring the intensity of any resulting coloration. The allergen activity may be gauged by the intensity of coloration.

6 Claims, 5 Drawing Sheets

U.S. PATENT DOCUMENTS 5,981,287 A 11/1999 Sinclair et al.
6,130,097 A 10/2000 Polzius et al.
6,350,586 B2 2/2002 Rao et al.

FOREIGN PATENT DOCUMENTS

| JP | 03259096 A | 11/1991 |
| WO | WO 96/30764 | 10/1996 |
| WO | WO 99/10736 | 3/1999 |

OTHER PUBLICATIONS

UK Search Report, dated Oct. 26, 2000.
PCT International Search Report dated Oct. 27, 2000, 4 pages.

* cited by examiner

ALLERGEN DETECTION APPARATUS

CROSS-REFERENCE TO RELATED APPLICATION

This application is a divisional of application Ser. No. 10/009,109, filed Dec. 7, 2001, pending.

BACKGROUND OF THE INVENTION

The present invention relates to allergen detection and, more particularly, to a method and apparatus for indicating allergen levels in dust samples.

STATE OF THE ART

It is estimated that up to 80% of the dust particles illuminated by incident sunlight and made visible to the naked eye in a domestic environment are derived from skin. In a warm environment, dust mites feed on skin-derived dust particles, breaking it down by using proteases in their digestive system. Such proteases are found in not insignificant levels in dust mite faeces, and it is now established that it is excreted proteases which act as allergens to individuals who are liable to have an allergic response to house dust. Concentrations of excreted protease are found in relatively high levels in carpets, bedding, pillows and mattresses, all of which provide a suitable environment for dust mites to thrive.

Dust mites are not the only source of proteases found in house dust. For example, proteases from cockroaches are also a source of allergens. Furthermore, it is possible that proteases from cat saliva become airborne as the saliva dries, for example, on the cat's fur. It is likely that such proteases also act as allergens to individuals who are allergic to house dust.

It is known to test house dust in order to determine quantitatively levels of the house dust mite allergen. According to one patent, U.S. Pat. No. 4,806,490, a dust sample is suspended in an aqueous-alcoholic alkali metal hydroxide solution to dissolve or leach out aromatic compounds such as guanine excreted by dust mites, and the resulting solution is mixed with an aromatic diazo compound. A reaction between the aromatic diazo compound and certain excreted aromatic compounds in the solution produces a color change, with the intensity of the new color being indicative of the level of excreted proteases in the house dust.

BRIEF SUMMARY OF THE INVENTION

According to a first aspect of the present invention, there is provided a method of determining allergen activity in dust, comprising: providing a dust sample; extracting from the dust sample at least one breakdown component of proteins or peptides; reacting the extracted at least one breakdown component with a colorimetric amine detection reagent; and determining or quantitatively measuring the intensity of any resulting coloration, the allergen activity being proportioned to the intensity of coloration.

The present applicant has appreciated that, in addition to proteases, dust mites excrete the by-products of skin breakdown, including amine compounds, amino acids and relatively small chain peptides, e.g., glycylglycine. In part, the present invention is directed to detecting some of the more abundant, and in some cases chemically less complex, by-products to give an indication of the allergen concentration, rather than targeting one specific compound (e.g., guanine) or type of compounds (e.g., aromatic compounds). This will enable individuals to test particular environments, e.g., individual rooms in a domestic situation to establish that environment's propensity for inducing an allergic response.

The method may further comprise exposing the dust sample to a protease substrate, the protease substrate having immobilized thereon proteins or peptides on which protease in the dust sample may act. The protease substrate may comprise a physical support, such as a matrix or membrane. Thus, in this way, the breakdown components of proteins or peptides will at least in part be generated in situ. This may be useful for increasing the concentration of such components, and hence improving subsequent quantitative coloration intensity measurements. If this technique is employed, the exposure time of the dust sample to the protease substrate may need to be controlled (e.g., set at 15 minutes). It is to be noted that, in such a process, the allergen is effectively being measured directly.

The method may further comprise adding a protease inhibitor to the dust sample to suppress activity of a specific protease prior to exposure to the protease substrate. In certain circumstances, it may be necessary to distinguish between dust mite protease and another protease (e.g., from cockroaches), since an individual may be more allergic to one than the other. Differentiation between the types of proteases present in the dust sample can be achieved by differential inhibition of certain specific proteases which may be present. For example, serine protease inhibitors may be used to inhibit specifically serine proteases. The serine protease inhibitors may be selected from the group consisting of organophosphates (e.g., diisopropylphosphofluoridate), sulphonyl fluorides (e.g., phenylmethylsulphonyl fluoride), coumarins (e.g., 3,4-dichloroisocoumarin) and peptide/protein inhibitors (e.g., peptide boronic acids and aprotinin, respectively). The use of serine protease inhibitors would allow dust mite allergens (e.g., cysteine proteases) to be detected more readily. On the other hand, cysteine protease inhibitors may be used if dust mite allergens were to be excluded from the test. The cysteine protease inhibitors may be selected from the group consisting of peptide diazomethanes (e.g., z-Phe-Ala-CHN2), peptide epoxides (e.g., E-64 and its derivatives), and cystatins.

In one embodiment of the method, the protease substrate is protease specific, with only a specific protease being able to act on the protein or peptide immobilized on the substrate. In this way, the protease substrate may be chosen to target a specific protease which may be present in the dust sample. If the protease is present in the sample, the specific proteins or peptides immobilized on the substrate will be broken down for subsequent detection. On the other hand, if the specific protease is absent, the proteins or peptides will remain intact and immobilized on the substrate.

The protease substrate may comprise a filter to facilitate extraction of mobile breakdown components of the proteins or peptides immobilized on the protease substrate. The filter may even act as a barrier to the passage of proteases therethrough. The breakdown components extracted from the dust sample may include amines, amino acids or peptides either from the dust sample or from the protease substrate.

The colorimetric amine detection reagent may be 2,4,6-trinitrobenzene sulphonic acid (hereinafter TNBSA).

The at least one breakdown component may be extracted by bringing the dust sample into contact with a surface active agent (surfactant). Any dust sample solid residues may be separated from the surfactant prior to reacting with the colorimetric amine detection reagent. The surfactant may be an aqueous solution comprising sodium dodecyl sulphate, possibly present in an amount of about ~5 wt %. The aqueous solution may be alkaline and may also comprise sodium hydrogen carbonate. The dust sample solid residues may be separated by filtration. Removing the solid residues facilitates accurate determination of the intensity of any coloration by reducing the amount of opaque material in the solution.

The intensity of any resulting coloration may be quantitatively determined by comparison with at least one reference color. The comparison may be with a plurality of different color references, each selected from the spectrum of colors or range of color hues attainable. The different color references may be selected to indicate at least three different kinds of allergen activity, perhaps corresponding to a macroscopic gradation such as low, medium and high activity.

The reaction mixture may be preserved by using a stopping agent, e.g., hydrochloric acid, after a preselected incubation or dwell time, e.g., about 2 minutes.

In order to give reproducible results, the dust sample may be of a predetermined size, e.g., by weight or by volume. The dust sample may be collected by a suction device, perhaps over a predetermined area or time. Variations in the dust sample size may be tolerated since the method represents a gross contamination test, so exact measurements of the dust samples are not necessarily essential.

In accordance with a second aspect of the invention, there is provided a method of determining allergen activity in dust, comprising: providing a dust sample; providing a protease substrate, the protease substrate having immobilized thereon proteins or peptides labeled with a chromogenic substance; exposing the protease substrate to the dust sample under conditions whereby any protease in the dust sample may act on the immobilized protein or peptide to produce mobile breakdown components labeled with the chromogenic substance; and quantitatively measuring the intensity of any resulting coloration, the allergen activity being proportional to the intensity of the coloration.

The method may further comprise adding a protease inhibitor to the dust sample to suppress activity of a specific protease prior to exposure to the protease substrate. As before, this will enable the specific protease to be excluded from becoming actively involved in the test, allowing other protease—perhaps present in lower concentrations—to be evaluated. For example, the inhibitor may be a cysteine protease inhibitor if protease allergens other than those from dust mites are to be evaluated.

In another embodiment of the invention, the protease substrate may be protease specific, with only a specific protease being able to act on the proteins or peptides immobilized on the substrate. In this way, the test may be tailored to evaluate a specific protease, regardless of whether different kinds of protease are present in the dust sample. For example, synthetic substrates with 4-nitroaniline and 2-naphthylamine (chromophores) can be used to distinguish between metalloproteases and aspartic proteases on the one hand (e.g., from cockroaches) and serine and cysteine proteases on the other hand (e.g., from dust mites).

The protease substrate may comprise a filter to facilitate extraction of mobile breakdown components labeled with the chromogenic substance. The filter may act as a barrier to all molecules which are larger than mobile breakdown components labeled with the chromogenic substance.

An example of a protein labeled with a chromogenic substance is azo-albumin. When reacted with a suitable protease, an azo-dye is released.

In accordance with a third aspect of the present invention, there is provided a method of determining allergen activity in dust, comprising: providing a dust sample; extracting from the dust sample at least one component selected from the group consisting of aliphatic amines and aliphatic amino acids; determining the relative concentration of the extracted at least one component; and providing an indication of allergen activity in dependence upon the relative concentration determined.

The relative concentration may be determined by employing a color indicator sensitive to aliphatic amines and amino acids. The color indicator may comprise TNBSA.

Any by-products of skin breakdown, particularly aliphatic amines and aliphatic amino acids, present in the dust sample may be linked to dust mite activity. The higher the levels of the by-products in the dust sample, the higher the dust mite activity may be assumed to be. High levels of dust mite activity will produce a correspondingly high amount of protease—the allergens which are largely responsible for providing the allergic reaction to house dust in certain individuals.

In accordance with a fourth aspect of the invention, there is provided a method of determining allergen-generation propensity in dust, comprising: providing a dust sample; exposing the dust sample to a protease able to break down proteins or peptides in human skin cells; reacting the exposed dust sample with a colorimetric amine detection reagent; and quantitatively measuring the intensity of any resulting coloration, the allergen-generation propensity being proportioned to the intensity of the coloration.

An individual may want to evaluate a dust sample to see whether it might support a high level of dust mite activity, even before the allergen levels have built up to significant, detectable levels. If the dust sample contains relatively high levels of human skin cells, the protease supplied will produce breakdown components which will react with the reagent and thereby be detected by color evaluation. By containing relatively high levels of human skin cells, the dust sampled could in theory support high concentrations of dust mites. Such information may be a useful warning to those individuals who are allergic to dust mite protease.

The calorimetric amine detection reagent may be 2,4,6-trinitrobenzene sulphonic acid. The intensity of any resulting coloration may be quantitatively measured by comparison with at least one reference color.

In accordance with another aspect of the present invention, there is provided apparatus for use in a domestic environment for determining indicating allergen levels. The apparatus may comprise a kit comprising a first chamber comprising a surfactant for extracting from a dust sample at least one breakdown component of proteins and peptides; a second chamber comprising a calorimetric amine detection reagent; means for quantitatively measuring the intensity of any coloration resulting from reacting the extract-containing surfactant and the calorimetric amine detection reagent; and means for indicating relative levels of allergen activity in the dust sample based on the quantitative measurement.

The apparatus may further comprise a filter for filtering dust sample solid residues from the surfactant before reacting with the calorimetric amine detection reagent, which may be TNBSA. One of the two chambers may have the capacity to receive the contents of the other chamber. Preferably, the second chamber has the capacity to hold the calorimetric amine detection apparatus and the surfactant.

The quantitative measuring means may comprise at least one color reference, against which the color of the solution may be compared. The indicating means may comprise a scale, e.g., low, medium and high activity, which is linked to the intensity of any coloration measured. For example, if the color of the solution is determined by eye as being about the same as the color reference, this could correspond to medium allergen activity. Divergence either side of the color reference would then correspond to low or high activity as appropriate.

The apparatus may further comprise a third chamber comprising a stopping reagent to limit the reaction between the extract-containing surfactant and calorimetric amine detection reagent, e.g., TNBSA.

BRIEF DESCRIPTION OF THE SEVERAL VIEWS OF THE DRAWINGS

An embodiment of the invention will now be described with reference to the accompanying drawings, in which.

DETAILED DESCRIPTION OF THE INVENTION

Figure 1:
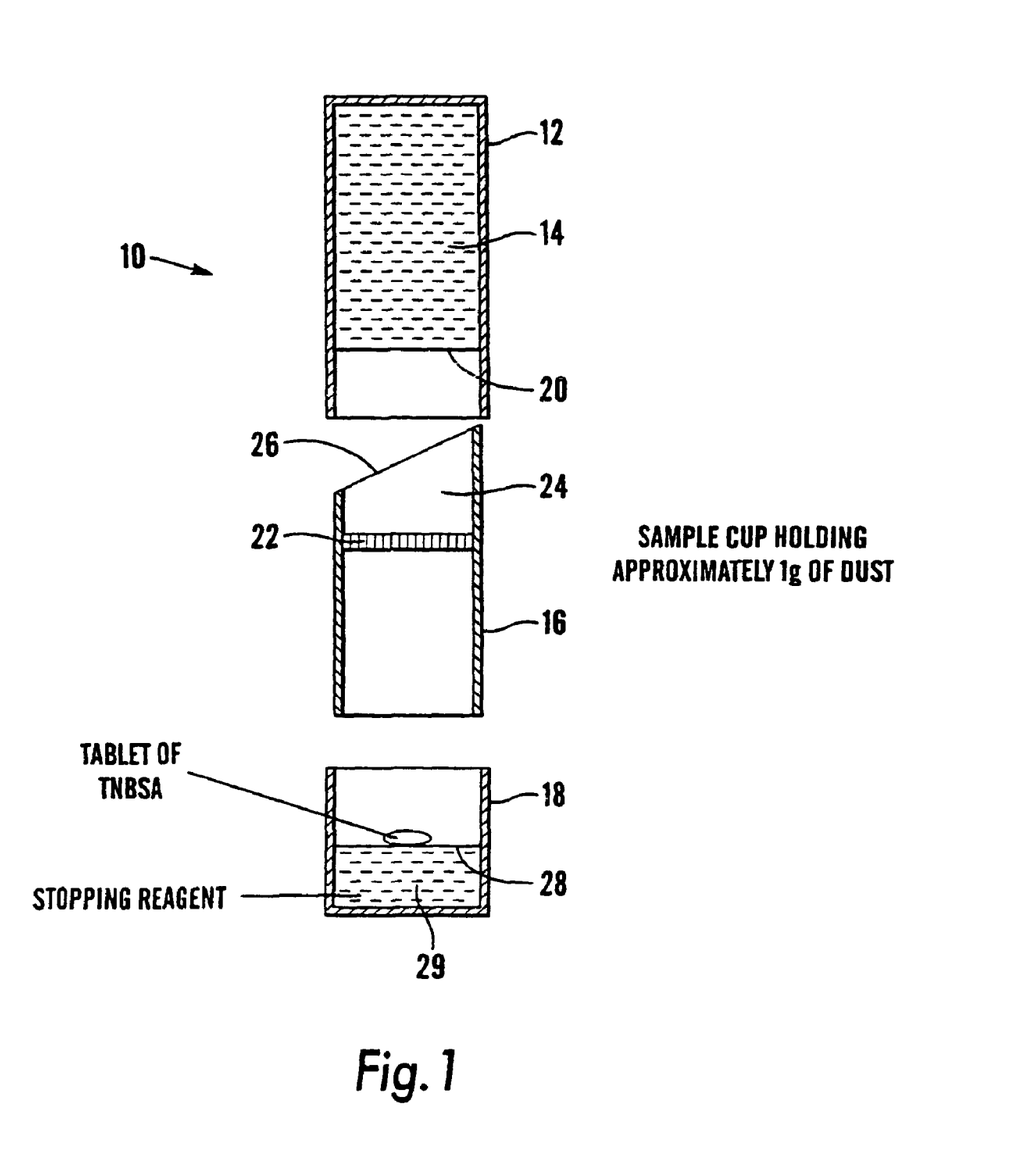
FIG. 1 shows schematically apparatus for determining dust mite activity in accordance with the present invention.

The apparatus 10 of FIG. 1 comprises three parts: an upper part 12 which contains in a first chamber 14 0.10 litres of a 0.1M solution of sodium hydrogen carbonate containing 5 wt % of sodium dodecyl sulphate; a middle part 16 which is a snug but sliding fit in both the upper part 12 and the remaining part; and a lower part 18 which contains a tablet of TNBSA and a stopping reagent of 1.0M hydrochloric acid. The solution in the first chamber 14 is sealed in the upper part 12 by a frangible seal 20. The middle part 16 comprises a filter 22 above which is provided a cup 24 for receiving a dust sample. The middle part 16 has a leading profile 26 which is pointed to facilitate breaking the frangible seal 20. A second chamber 27 (FIG. 2) is formed by the middle and lower parts. The lower part 18 includes a frangible seal 28 disposed between the tablet of TNBSA and the stopping reagent which is sealed in a third chamber 29.

Figure 2:
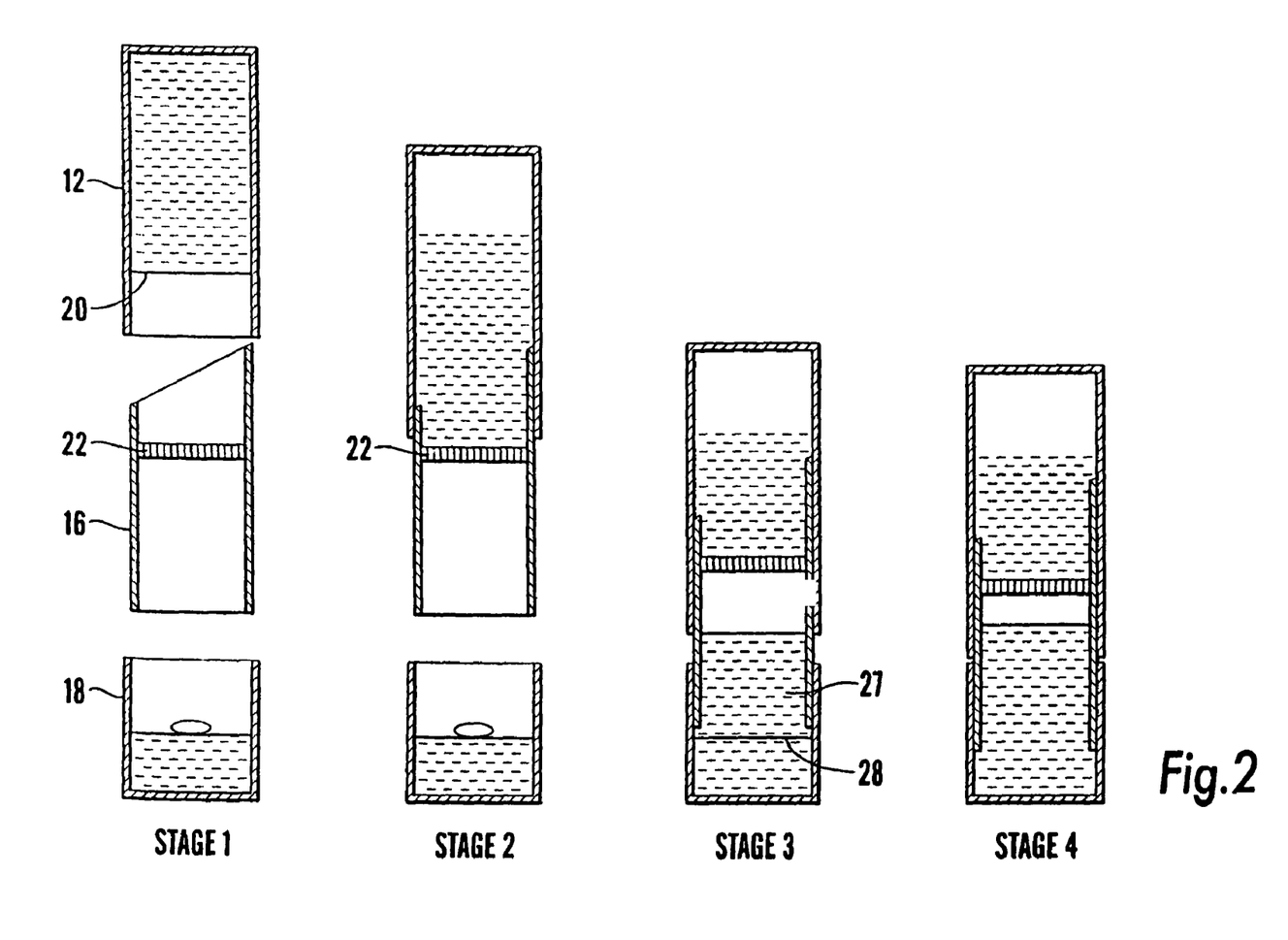
FIG. 2 shows schematically the use of apparatus shown in FIG. 1.

The use of the apparatus 10 is now described in stages with reference to FIG. 2:

Stage 1 A sample of dust of predetermined size is placed in cup 24.

Stage 2 The middle part 16 is inserted into the upper part 12, such that the profile 26 ruptures the seal 20.

Stage 3 The solution in the first chamber comes into contact with the dust sample. Any chemicals including amines, amino acids and peptides present in the dust sample are extracted and pass through filter 22 and into the second chamber 27 where they come into contact with the tablet of TNBSA.

Stage 4 After about 2 minutes, the middle part 16 is pushed far enough into the lower part 18 to rupture seal 28, enabling the stopping reagent in the third chamber 29 to prevent further reaction. The color of the resulting solution is compared with a color key which is calibrated to give an indication of the level (e.g., low, medium or high) of dust mite activity in the dust sample.

EXAMPLE

A dust sample was collected from an old mattress (where dust mite activity may be expected to be high), and a blank sample and test samples of GlycylGlycine in varying concentrations (20-200 micrograms) were used as controls. The dust, blank and test samples were washed with 0.1M $NaHCO_3$ 0.5M NaCl (ph 8.3) and then tested with ThBSA of various concentrations e.g., diluted to 1 part in 10, 1 part in 50 and 1 part in 100. It was found that a dilution of 2 parts in 50 was the optimum dilution for sensitivity and blank color. Using such a dilution, the experiment yielded visual results for both the dust and all test samples, but not the blank sample. The visual results could then be assessed and compared to give an indication of dust mite activity in the old mattress.

Figure 3:
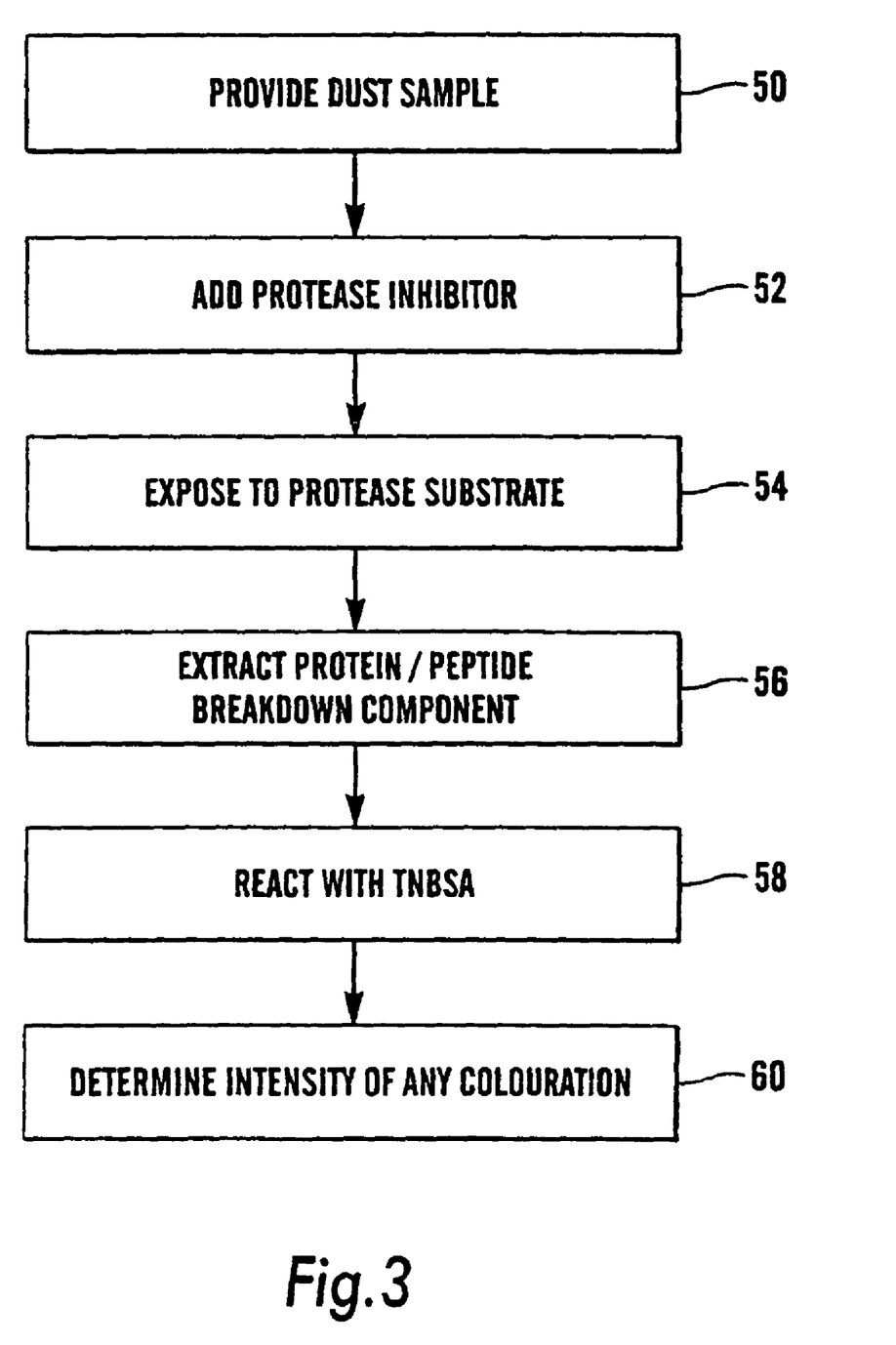
FIG. 3 is a flow chart illustrating one method of determining allergen levels according to the invention.

The method used in the example may be summarized and developed with reference to FIG. 3. A dust sample is provided at step 50, possibly by using a suction device to collect dust from furniture or carpets. A protease inhibitor (e.g., serine protease inhibitor) is added at step 52) to enable a particular protease (e.g., cysteine protease) to be targeted. Next, at step 54, the dust sample is exposed to a protease substrate which is susceptible to the proteases present. Protein or peptide breakdown components from the dust sample or protease substrate are then extracted at 56 and are reacted at 58 with the calorimetric amine detection reagent (TNBSA). The presence of free amino groups causes an orange-colored product, the intensity of which is measured at 60 to give an indication of allergen levels.

Instead of using a protease inhibitor (step 52), the protease substrate may be selected to be protease specific. In other words, the protease substrate may contain proteins or peptides which require the presence of specific proteases under evaluation before yielding detectable breakdown components.

An alternative method is illustrated in FIG. 4, and again starts with the provision of a dust sample (again step 50). A protease-specific substrate is provided at 70, the substrate having immobilized thereon proteins or peptides which require specific proteases before yielding breakdown components. The immobilized proteins or peptides are also labeled with a chromogenic substance. At step 72, the substrate is exposed to the dust sample. The presence of the specific proteases in the sample will break down the immobilized proteins or peptides, releasing the chromogenic substance, causing coloration of the solution. The intensity of the coloration is measured at 74 to give an indication of allergen levels.

Figure 4:
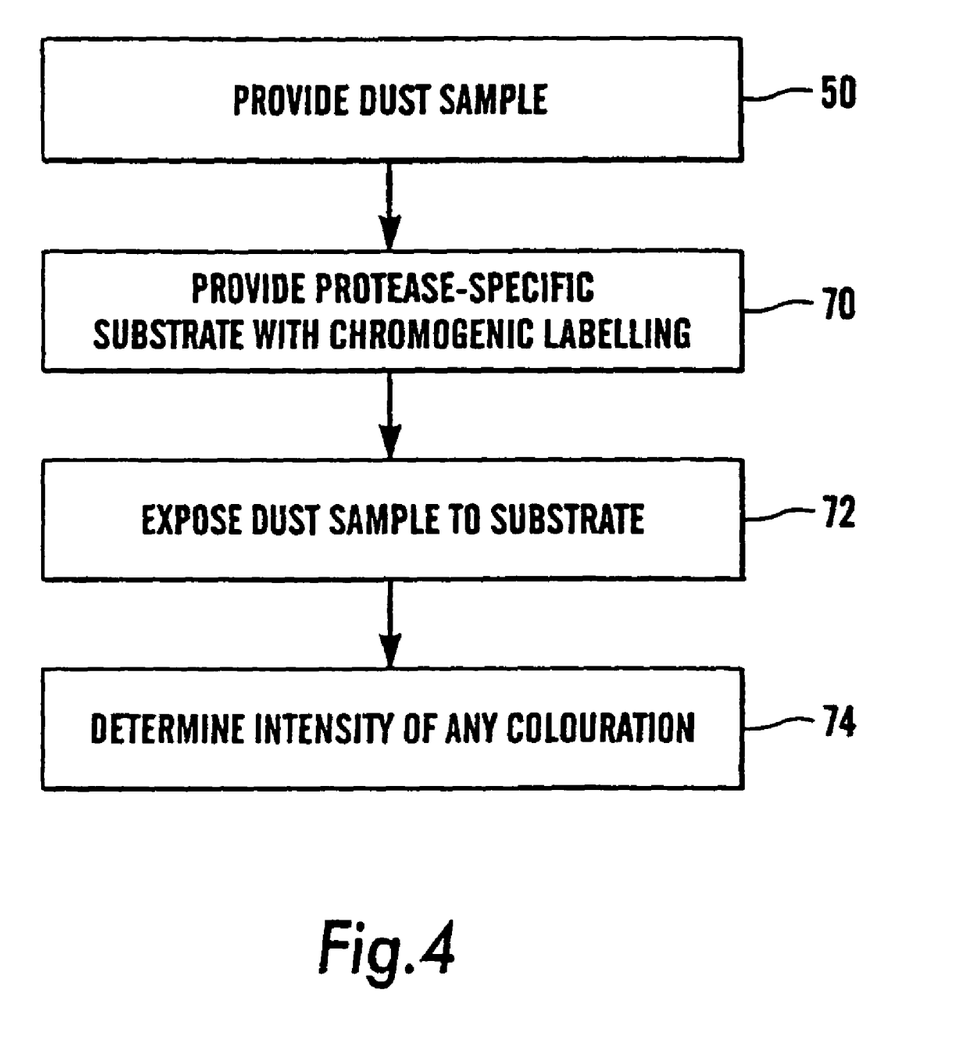
FIG. 4 is a flow chart illustrating another method embodying the invention.

Instead of using a protease-specific substrate (step 70), the protease substrate may be nonspecific, but still labeled with the chromogenic substance. If a specific protease is still to be targeted, this may be accomplished using protease inhibitors (step 52 of FIG. 3).

Figure 5A:
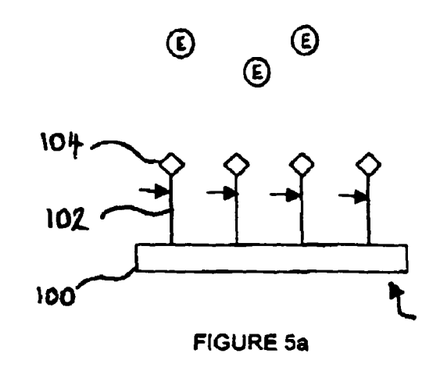
FIGS. 5a and 5b show schematical use of a protease detection apparatus according to one aspect of the invention.
Figure 5B:
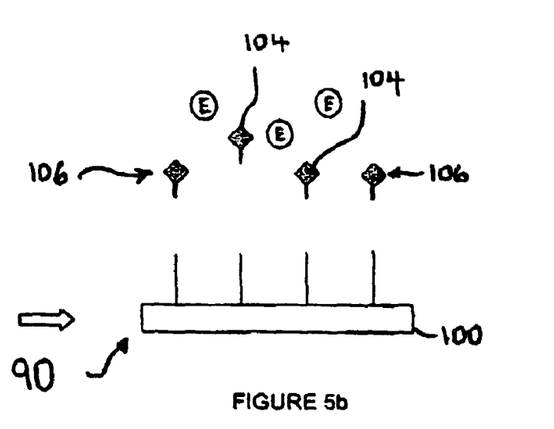

FIGS. 5a and 5b illustrate schematically the use of protease detection apparatus 90, comprising a substrate 100 having immobilized thereon proteins or peptides 102 labeled with a chromogenic substance 104. The substrate 100 comprises filter paper, and the proteins or peptides 102 are either chemically attached to the substrate 100 or physically attached thereto (e.g., by applying in liquid form and subsequently drying). FIG. 5a illustrates the substrate 100 immediately prior to exposure to a liquid sample containing protease E. When exposed to the protease E, the proteins or peptides 102 are chemically broken down, releasing mobile breakdown components 106 labeled with the chromogenic substance 104 as shown in FIG. 5b. The chromogenic substance 104 present in the mobile breakdown components 106 gives rise to a color change in the liquid sample and, hence, provides a visible indication of the presence of protease in the liquid sample. The substrate 100 may be used to filter the liquid sample after the proteins or peptides have been exposed to the protease E.

What is claimed is:

1. A protease activity detection apparatus that determines allergen levels in a dust sample, comprising:

a substrate;

proteins or peptides labeled with a chromogenic substance attached to and immobilized on the substrate, the immobilized proteins or peptides having a structure that is cleaved by protease found in the dust sample to produce mobile breakdown products of an enzyme reaction labeled with the chromogenic substance and a resultant colour change;

a surfactant that extracts the breakdown products from the substrate;

an upper part having an internal chamber with an open end;

a frangible seal that seals the surfactant within the internal chamber, the frangible seal being set back into the chamber from the open end;

a middle part, having an internal passageway extending between opposing ends, the substrate dividing the internal passageway and wherein an outside diameter of a first end of the middle part forms a snug but sliding fit with an inside diameter of the open end; and a lower part containing a calorimetric amine detection reagent, a diameter of the lower part forming a snug but sliding fit with a second end of the middle part.

2. The apparatus according to claim 1, in which proteins labeled with the chromogenic substance comprise azo-albumin.

3. The apparatus according to claim 1, further comprising a filter to facilitate extraction of mobile breakdown products labeled with the chromogenic substance by acting as a barrier to all molecules which are larger than the mobile breakdown components.

4. The apparatus as defined in claim 1 to determine allergen levels in a dust sample further comprising at least one color reference, against which an intensity of any color change may be compared.

5. The apparatus as defined in claim 2 to determine allergen levels in a dust sample further comprising a scale, which is linked to the intensity of any color change.

6. The apparatus as defined in claim 5 to determine allergen levels in a dust sample further comprising the scale having a high, medium and low activity colors.

* * * * *